United States Patent
Grotheer et al.

(10) Patent No.: US 10,576,309 B2
(45) Date of Patent: Mar. 3, 2020

(54) METHOD OF REDUCING PERSPIRATION

(71) Applicant: BEIERSDORF AG, Hamburg (DE)

(72) Inventors: Elke Grotheer, Boenningstedt (DE); Frank Lehmbeck, Norderstedt (DE); Robert Klauck, Reinbek (DE); Nadia Lund, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 16/065,082

(22) PCT Filed: Dec. 9, 2016

(86) PCT No.: PCT/EP2016/080376
§ 371 (c)(1),
(2) Date: Jun. 21, 2018

(87) PCT Pub. No.: WO2017/108445
PCT Pub. Date: Jun. 29, 2017

(65) Prior Publication Data
US 2018/0326229 A1     Nov. 15, 2018

(30) Foreign Application Priority Data

Dec. 23, 2015 (DE) .................. 10 2015 226 630

(51) Int. Cl.
| | | |
|---|---|---|
| A61Q 15/00 | (2006.01) | |
| A61K 8/25 | (2006.01) | |
| A61K 8/365 | (2006.01) | |
| A61K 8/02 | (2006.01) | |
| A61K 8/04 | (2006.01) | |
| A61K 8/06 | (2006.01) | |
| A61K 8/26 | (2006.01) | |
| A61K 8/28 | (2006.01) | |
| A61K 8/34 | (2006.01) | |

(52) U.S. Cl.
CPC ............ *A61Q 15/00* (2013.01); *A61K 8/0229* (2013.01); *A61K 8/042* (2013.01); *A61K 8/064* (2013.01); *A61K 8/25* (2013.01); *A61K 8/365* (2013.01); *A61K 8/044* (2013.01); *A61K 8/26* (2013.01); *A61K 8/28* (2013.01); *A61K 8/34* (2013.01); *A61K 2800/882* (2013.01)

(58) Field of Classification Search
CPC ...... A61K 8/064; A61K 8/042; A61K 8/0229; A61K 8/25; A61K 8/365; A61K 8/27; A61K 8/044; A61K 8/34; A61K 8/28; A61K 2800/882; A61Q 15/00
See application file for complete search history.

(56) References Cited

U.S. PATENT DOCUMENTS

| | | | |
|---|---|---|---|
| 4,921,694 A | 5/1990 | Hoppe | |
| 5,169,029 A | 12/1992 | Behar | |
| 5,318,778 A | 6/1994 | Schmucker | |
| 5,648,067 A | 7/1997 | Dillenburg | |
| 5,718,888 A | 2/1998 | Klier | |
| 5,884,759 A | 3/1999 | Gueret | |
| 6,220,483 B1 | 4/2001 | van der Heijden | |
| 8,021,064 B2 | 9/2011 | Gueret | |
| 2004/0149775 A1 | 8/2004 | Chen | |
| 2006/0054634 A1 | 3/2006 | Mekata | |
| 2006/0171973 A1 | 8/2006 | Withiam | |
| 2006/0213927 A1 | 9/2006 | Behar | |
| 2008/0221003 A1* | 9/2008 | Meine | C11D 3/505 510/103 |
| 2009/0108021 A1* | 4/2009 | Hansen | B65D 83/202 222/1 |
| 2016/0008263 A1* | 1/2016 | Mendoza | A61K 8/375 424/401 |
| 2017/0007531 A1 | 1/2017 | Bastos | |

FOREIGN PATENT DOCUMENTS

| | | |
|---|---|---|
| CH | 470183 A | 3/1969 |
| DE | 3740186 A1 | 1/1989 |
| DE | 3938140 A1 | 8/1991 |
| DE | 4009347 A1 | 9/1991 |
| DE | 4204321 A1 | 8/1993 |
| DE | 4229707 A1 | 3/1994 |
| DE | 4229737 A1 | 3/1994 |
| DE | 4237081 A1 | 5/1994 |
| DE | 4309372 A1 | 9/1994 |
| DE | 4324219 A1 | 1/1995 |
| DE | 10109063 A1 | 9/2002 |
| DE | 102004063728 A1 | 7/2006 |
| DE | 202007003056 U1 | 7/2007 |
| DE | 202008014407 U1 | 2/2009 |
| EP | 0461010 A1 | 12/1991 |
| EP | 0816253 A1 | 1/1998 |
| EP | 0958062 A1 | 11/1999 |
| FR | 2852928 A1 | 10/2004 |
| FR | 2900550 A1 | 11/2007 |
| FR | 2977151 A1 | 1/2013 |
| WO | 9834733 A1 | 8/1998 |
| WO | 2015121667 A1 | 8/2015 |
| WO | WO 2015121667 A1 * | 8/2015 |

OTHER PUBLICATIONS

Wilke K. et al., Int J Cosmet Sci. 2007 29(3)169-79.
Shelley WB and Hurley HJ, Acta. Derm. Venereol. (1975) 55: 241-60.
Reller HH and Luedders WL, in: Advances in Modem Toxicology, Dermatoxicology and Pharmocology, F.N. Marzulli and H.I. Maibach, Eds. Hemisphere Publishing Company, Washington and London (1977) vol. 4: 1-5.

* cited by examiner

*Primary Examiner* — Blessing M Fubara
(74) *Attorney, Agent, or Firm* — Abel Schillinger, LLP

(57) ABSTRACT

Cosmetic product comprising a two-chamber container for application of cosmetic preparations, characterized in that the first chamber contains a preparation comprising silicic acid (phase 1) and the second chamber contains a preparation comprising an alkaline compound (base) (phase 2).

20 Claims, No Drawings

METHOD OF REDUCING PERSPIRATION

BACKGROUND OF THE INVENTION

1. Field of the Invention

The invention relates to a method for reducing or preventing apoeccrine sweating by applying two cosmetic part preparations, characterized in that the time period between mixing the part preparations and applying the mixture to the skin is not more than five minutes and wherein one part preparation comprises an alkali metal silicate and the second part preparation comprises one or more pH regulators.

2. Discussion of Background Information

Sweat denotes an aqueous secretion secreted by human skin via so-called sweat glands. There are three types of sweat glands in the skin, namely apocrine, eccrine and apoeccrine sweat glands (Int J Cosmet Sci. 2007 June; 29(3):169-79).

In humans, the eccrine sweat glands are distributed practically over the entire body and can produce considerable amounts of a clear, odorless secretion consisting of water to an extent of over 99%. By contrast, the apocrine sweat glands occur only in the hairy body areas of the underarm region and genital region and also on nipples. They produce low amounts of a milky secretion which contains proteins and lipids and is chemically neutral.

Sweating, also referred to as perspiration, is an effective mechanism of radiating excess heat and thus of regulating body temperature. What is especially used for this purpose is the high-volume aqueous secretion of the eccrine glands, which can produce up to 2-4 liters per hour, or 10-14 liters per day, in adults.

Furthermore, a signaling effect via olfaction is attributed to sweat—especially to the secretion of the apocrine sweat glands. In humans, apocrine sweat is especially important in connection with emotional or stress-related sweating.

Cosmetic antiperspirants or deodorants are used to eliminate body odor or to reduce the development thereof. Body odor develops when inherently odorless fresh sweat is decomposed by microorganisms such as, for example, staphylococci and corynebacteria.

In everyday language, there is not always a clear separation between the terms "deodorant" and "antiperspirant". On the contrary—especially also in the German-speaking world—products for use in the underarm region are sweepingly referred to as deodorants. This is done regardless of whether there is also an antiperspirant effect.

Antiperspirants (APs) are antisweating means which are intended to prevent the secretion of sweat in the first place—in contrast to deodorants, which generally prevent a microbial decomposition of sweat that has already formed.

In contrast to antiperspirants, pure deodorants do not actively influence sweat secretion, but instead merely regulate or influence body odor or underarm odor (odor improver). Different modes of action form the basis of customary cosmetic deodorants.

Common mechanisms of action in relation thereto are antibacterial effects, as also exhibited by noncolloidal silver for example, odor neutralization (masking), influencing of bacterial metabolisms, pure perfuming as well as the use of precursors of certain perfume components which are converted to fragrant substances by enzymatic reactions.

Sweat odor consists to a large extent of branched-chain fatty acids which are released from odorless sweat by bacterial enzymes. Traditional active deodorant ingredients counteract this by reducing the growth of bacteria. However, in many cases, the substances used in this connection act nonselectively even against useful skin pathogens and can lead to skin irritations in sensitive individuals.

Aluminum salts or aluminum/zirconium salts are especially used as traditional antiperspirants. They inhibit sweating by clogging of the excretory ducts of the sweat glands, by precipitating locally together with skin-endogenous proteins and thus resulting in so-called plugs. Therefore, what can occur is congestion of the sweat within the gland.

The effect of antiperspirants based on Al salts against thermal sweating under normal physiological conditions has been thoroughly investigated.

Whether this blockage is caused by denaturation of keratin or by clumping of corneocytes in the sweat gland ducts (Shelley W B and Hurley H J, Acta. Derm. Venereol. (1975) 55: 241-60), or by formation of an ACH/AZG gel (Reller H H and Luedders W L, in: Advances in Modern Toxicology, Dermatoxicology and Pharmocology, F. N. Marzulli and H. I. Maibach, Eds. Hemisphere Publishing Company, Washington and London (1977) Vol. 4: 1-5), formed by neutralization in the sweat gland duct, is still open to question.

However, the known blockage thus achieved is only effective for a short time. Heavy sweating or cleaning of the underarm as part of the normal body-washing routine cancels out the clogging again and thus also the antiperspirant effect. However, the resulting necessity of applying antiperspirant (AP) products at least once daily may lead to skin irritations, especially after shaving or in or on skin areas that are already damaged.

Furthermore, aluminum salts such as aluminum chlorohydrates can cause skin damage in the event of frequent use and in sensitive individuals. Furthermore, the use of the aluminum salts can lead to discolorations of textiles which come into contact with the antiperspirant.

The additional use of antimicrobial substances in cosmetic antiperspirants can reduce the bacterial flora on the skin. In this connection, only the odor-causing microorganisms should ideally be reduced in an effective manner. Sweating itself is not influenced as a result; ideally, only the microbial decomposition of sweat is temporarily stopped.

Customarily, antiperspirants (APs) and deodorants are provided in various product forms, with roll-ons, pump sprays and aerosols dominating in Europe and deodorant sticks being more common in the USA, Central America and South America. Both anhydrous (suspensions) and aqueous products (aqueous/alcoholic formulations, emulsions) are known.

A satisfactory deodorant must satisfy the following requirements: 1) conservation of the natural biology of the skin 2) odor neutrality 3) efficacy only with respect to deodorization, i.e., only avoidance and/or elimination of body odor 4) avoidance of the formation of resistant bacterial strains 5) harmlessness in the event of overdosage or other unintended use 6) good cosmetic use 7) easy handling (e.g., as liquid) and universal applicability in a wide variety of different cosmetic and external preparations 8) excellent skin and mucosa compatibility 9) use of environmentally friendly substances.

In addition to liquid deodorants and antiperspirants, solid preparations are also known and common, for example powders, powder sprays as, genital hygiene products.

The nature of the composition of cosmetic preparations finds its natural limits which are determined by the compatibility of the individual components with one another and the stability of individual components in the carrier medium.

The combination of differently charged polymers or surfactants also results in clumping and precipitation in cosmetic formulations.

There has been no lack of attempts to make such preparations accessible to the consumer. The subcomponents of the formulations are then usually packaged and stored separately. For this purpose, so-called dual chamber packaging is generally used in which the part preparations are stored in separate storage vessels and which can be withdrawn simultaneously from the package container via a common opening.

FR 2852928 discloses a dual chamber container in which the product is withdrawn by means of two pumps in such a manner that the preparations are mixed only in the output channel.

A dual chamber container is known from US 20040149775 in which the chambers are interchangeable. The preparations are also dispensed here by means of two pumps via a common output channel in which the mixing of the components takes place.

EP 958062 discloses a dual chamber packaging with pumps arranged concentrically.

FR 2900550 discloses various dual chamber packagings having a flocked applicator surface. The mixing of the components only occurs directly during application.

EP 0461010 discloses a dual chamber aerosol packaging in which the components are only mixed prior to emission from the nozzle.

Multi-chamber containers are known from US 20060054634 which function according to the bag-in-can principle and in which the at least two chambers are composed of interconnected bags.

The use of dual chamber packaging is still unknown in deodorant and/or antiperspirant products since the aluminum-containing formulations used to date, in which ACH is present as solid, are exceptionally stable.

A disadvantage of the aluminum salts used to date for sweat inhibition is the currently still incompletely explained long-term toxicity. Aluminum has been suspected for a long time of promoting or triggering neurodegenerative diseases such as dementia, especially Alzheimer's disease. In addition, aluminum is associated with the development of breast cancer. To date, there is no conclusive evidence that aluminum-containing antiperspirants acting via the skin are involved. In the case of intact skin, the maximum permitted uptake amounts cannot be reached.

However, in view of the data situation, the abandonment of aluminum-containing antiperspirants is advantageous, meaning that the industry is desperately seeking aluminum-free alternatives.

On the basis of this problem, it is desirable to provide products which achieve an antiperspirant effect without use of Al salts.

One alternative to Al salts is represented by short-chain silicates in the form of silicic acids, which can reliably suppress sweating.

WO 2015/121667 discloses acidic, stabilized silicic acids as antiperspirant active ingredients. The effect is based on polymerization of acidic silicic acids induced by an increase of the pH. This increase is brought about by contact with skin and perspiration. The stabilizers required prolong the polymerization of the silicic acid. The acidic, stabilized silicic acids are produced in a specific process.

A disadvantage of the acidic silicic acid produced in this way is its incompatibility with many of the customary cosmetic auxiliaries such as emulsifiers, surfactants and oils. As a result, it is virtually impossible to produce in a stable manner customary formulation forms such as emulsions.

Since pH levels below 3.0 are physiologically incompatible, it is necessary to find preparation forms in which the pH is at least 3.0 and in which there is no gel formation or precipitation of amorphous colloids (silica sol). The irritation potential is very highly dependent on how strongly the applied preparation is buffered. If the preparation is only weakly buffered, the pH on the skin very rapidly increases to a physiologically acceptable degree (or decreases in the case of basic preparations). In the case of strongly buffered preparations, the pH of the preparation must be as close as possible to the compatible pH range of 5 to 8.

FR 2977151 describes the use of alkaline silicates as antiperspirant active ingredients.

The known silicic acids or silicates have the disadvantage that they have to be applied to the skin either as acidic or alkaline components. This can lead to skin irritations and incompatibilities. It is therefore advantageous to use products having a pH that is kind to the skin and therefore to satisfy consumer requirements of a highly effective and at the same time skin-friendly or even nurturing antiperspirant. It is also advantageous to avoid a special complex method for producing the active substances.

Therefore, it would be desirable to provide an antiperspirant product which does not display the aforementioned disadvantages and secondary effects, more particularly of the ACH-containing preparations.

Furthermore, it would be desirable to provide an antiperspirant product which makes a contribution to the prior art and represents an alternative to the known preparations, more particularly ACH-containing preparations.

In particular it is also desirable to provide an antiperspirant product that does not cause any skin irritation after application, i.e. that has a physiologically acceptable pH.

It is thus a further object of the present invention to develop a product which is suitable as a base for cosmetic deodorants or antiperspirants and does not have the disadvantages of the prior art, particularly characterized by good skin compatibility.

In particular, it is an object of the invention to provide silicate-containing antiperspirant preparations comprising at least one alkali metal silicate in combination with one or more pH regulator(s) and having a physiologically compatible pH.

SUMMARY OF THE INVENTION

After all this, it was surprising and unforeseeable that silicate-containing preparations having a pH of at least 4 to 8, comprising one or more alkali metal silicates and one or more pH regulator(s), are suitable for use as skin-compatible antiperspirants, i.e. for reducing or preventing apoeccrine sweating, if the components are mixed only shortly before application, and thereby overcoming the disadvantages of the prior art, the lack of stability of physiologically compatible silicate preparations.

It was astonishing that, by separately providing a silicate-containing preparation and a pH regulator in a dual chamber packaging, mixing the silicate-containing preparation with the pH regulator only shortly before or during dispensing and/or application, are not only outstandingly suitable for cosmetic purposes but, moreover, are more effective and milder than the use of stable compositions of the prior art.

The invention therefore relates to a method for reducing or preventing apoeccrine sweating, characterized in that two cosmetic part preparations are mixed in a first step and the mixture is applied to the skin in a second step, wherein the time period between mixing the part preparations and applying the mixture to the skin is not more than five minutes and wherein one part preparation comprises an alkali metal silicate and the second part preparation comprises one or more pH regulator(s).

The invention is suitable for applying cosmetic preparations via a cosmetic product comprising a dual chamber container, characterized in that one chamber contains a preparation comprising at least one alkali metal silicate (phase 1) and the second chamber contains a preparation comprising at least one pH regulator (phase 2), wherein during application the contents of the first and second chambers are simultaneously withdrawn from the chambers and phases 1 and 2 are mixed on dispensing or shortly before dispensing.

Rapid pH reduction is crucial for successful formation of the silicates or silicic acids. If pH reduction is carried out too slowly, silicic acids having a very high molecular weight and having no antiperspirant activity are formed, culminating in gel formation.

In connection with the process according to the invention, it is always postulated that in the mixture of phase 1 containing silicate and phase 2, the silicon compounds are further present as silicates. Depending on the pH of the mixture, silicic acids may also be present however. Silicic acid is a very weak acid having a pKa1=9.51; pKa2=11.74. That is to say, in the pH range according to the invention, the 'silicon' is present predominantly as silicic acid and only a little as silicate.

The mixtures produced according to this process are only briefly stable which is why application of this AP formulation directly after mixing is required. If the mixing does not take place rapidly enough or the application is too late, it can then result in polymerization of the silicic acid (gel formation). This then no longer has any AP effect.

The invention also encompasses accordingly the use of silicates as antiperspirant active ingredient, particularly in cosmetic and/or dermatological preparations that can be preferably applied topically, wherein the pH of the preparation is only adjusted to a physiologically compatible level prior to application, the pH of the applied preparation being in particular not less than 4.

The pH of the applied mixture should be between 4 and 8, preferably between 5.1 and 6.9, particularly preferably between 5.3 and 6.7.

The mixtures according to the invention exhibit an antiperspirant effect even without a further change to the pH.

The silicates are selected from:
alkali metal silicate, in particular sodium silicate, potassium silicate, water glass, particularly preferably sodium silicate.

The silicates are advantageously silicate-containing aqueous solutions of silicates, wherein the silicon concentration is in the range of 1 to 10 mol/l, preferably in the range of 4 to 8 mol/l.

Water glass refers to glassy, i.e. amorphous, water-soluble sodium, potassium and lithium silicates, solidified from a melt, or their aqueous solutions. Depending on whether sodium, potassium or lithium silicates are predominantly present, they are referred to as sodium water glass, potassium water glass or lithium water glass.

To produce solid water glasses (solid glasses), mixtures of quartz sand and potassium carbonate (for potassium water glass) or sodium carbonate (for sodium water glass) are melted with CO2 elimination at 1100° C. to 1200° C. [5]:

The general formula M2O.nSiO2 of industrially important water glasses is approximately in the range between n equal to 1 to 4, depending on the composition of the mixtures. For a water glass, in general the molar or mass ratio of SiO2 to Na2O or SiO2 to K2O are specified. Sodium water glass (see also sodium silicates) having the molar ratio 3.4 to 3.5 constitutes the most important quantitative proportion.

The cooled glass is ground to a powder. By dissolving in water at high temperatures (e.g. 150° C. at 5 bar pressure), liquid water glass (liquid glass) is obtained therefrom as a clear, colloidal alkaline solution or alkaline gel (gelatinous to solid mass).

The silicate-containing solutions thus obtained are strongly alkaline and have a pH of >=10.

An alkaline solution of commercially available sodium silicate (water glass) or potassium silicate (potassium water glass). This has, for example, an Si content of 6.25 mol/l, which corresponds to ca. 10.6% $Na_2O$ and ca. 26.5% $SiO_2$.

The use of silicate solutions is very much simpler than the silicic acids known from WO 2015/121667, since silicate solutions are stable virtually indefinitely and the acidic silicic acids firstly have to be produced from silicates by means of a process that is complicated to control.

The lowering of the pH is achieved with the aid of pH regulators contained in phase 2.

pH regulators according to the invention can be buffer systems which are either added in aqueous solution or in the anhydrous state. The buffer systems may consist of bases such as, e.g.: 2-aminobutanol, 2-(2-aminoethoxy)ethanol, aminoethyl propanediol, aminomethyl propanediol, aminomethyl propanol, aminopropanediol, bis-hydroxyethyl tromethamine, butyl diethanolamine, butylethanolamine, dibutyl ethanolamine, diethanolamine, diethyl ethanolamine, diisopropanolamine, dimethylamino methylpropanol, dimethyl isopropanolamine, dimethyl MEA, ethanolamine, ethyl ethanolamine, isopropanolamine, methyl diethanolamine, methylethanolamine, triethanolamine, triisopropanolamine, tromethamine, polyethylenimine, tetrahydroxypropyl ethylenediamine, ammonia and cosmetically acceptable acids and have a pH of 2 to 6.

Examples of acids particularly suitable for buffer preparation are citric acid, lactic acid, tartaric acid, fatty acids, phosphoric acid, phosphonic acids, polyacrylic acids, succinic acid, malic acid, oxalic acid, amino acids.

It is also possible to use unbuffered acids as pH regulators and especially suitable are mineral acids such as hydrochloric acid, sulfuric acid or phosphoric acid, the anions of which are physiologically compatible and can be easily kept in solution. However, pH reduction can also be achieved with any other acids, provided that they a) can suitably lower the pH and b) the salts thereof, especially the sodium salt, are physiologically compatible and do not cause skin irritations. Preferably, hydrochloric acid is used for lowering pH.

By means of rapid mixing of phase 1 and phase 2, the pH of the overall mixture is lowered to a pH between 4 and 8, preferably between 5.1 and 6.9, particularly preferably between 5.3 and 6.7.

In addition, phase 1 (silicate-containing phase) and phase 2 (pH regulator-containing phase) may comprise further constituents customary for cosmetic preparations such as perfume, rheology modifiers, solubilizers, care substances, colorants, skin-care components.

Advantageously, one or both components comprise stabilizers which delay polymerization on the skin.

The stabilizers are selected from
group A: cis-3-hexenol (CAS 928-96-1), terpineol (CAS 8000-41-7), linalool (CAS 78-70-6), tetrahydrolinalool (CAS 78-69-3), triethyl citrate (CAS 77-93-0), 2-isobutyl-4-hydroxy-4-methyltetrahydropyran (CAS 63500-71-0), hexyl salicylate (CAS 6259-76-3), phenylethyl alcohol (CAS 60-12-8), 3-methyl-5-phenyl-1-pentanol (CAS 55066-48-3), 2,6-dimethyl-7-octen-2-ol (CAS 18479-58-8), benzyl salicylate (CAS 118-58-1), geraniol (CAS 106-24-1), citronellol (CAS 106-22-9) and ethyl linalool (CAS 10339-55-6);
group B: alcohols and diols and
group C: substances having at least three hydroxyl groups.

Particularly advantageous are stabilizers from the group consisting of linalool (CAS 78-70-6), benzyl salicylate (CAS 118-58-1), geraniol (CAS 106-24-1) and citronellol (CAS 106-22-9).

Especially advantageous stabilizers from group B are: ethanol, 2-propanol, PEG 8, triethylene glycol, methylphenylbutanol, decanediol, polyglyceryl-2 caprate, oxalic acid.

Especially advantageous stabilizers from group C are: sucrose (mannose, mannitol), glycerol, pentaerythritol, threitol, erythritol, hyaluronic acid.

The topical application of mixtures of phase 1 and phase 2 comprising silicates in combination with one or more pH regulators and stabilizers selected from group A, B and/or C enables the reduction or prevention of stress sweating.

In the context of the invention, antiperspirant effect is understood to mean the possibility of reducing or preventing sweating. This means that silicates act as sweat inhibitors and reduce sweating and thus indirectly also sweat odor.

By lowering the pH of the silicate-containing preparation on or prior to dispensing and application, preparations are provided which have a high physiological compatibility.

The mixing of silicate-containing preparation with the pH lowering acid only prior to dispensing from a dual chamber packaging makes possible the use of silicate-containing preparations as compatible antiperspirants.

Products with silicates according to the invention enable a sweat-inhibiting effect at the same order of magnitude as known and proven active antiperspirant ingredients, with the required concentration of silicates being very much lower than when using ACH.

The pH lowering just prior to application also eradicates the disadvantages detailed such as skin irritation due to excessively high or low pH of pure silicate solutions or unstabilized silicic acid solutions, and the toxicity of aluminum compounds that is under discussion.

The phases of the process according to the invention or the process-converting products therefore preferably comprise, besides a silicate-containing preparation, no further active antiperspirant substances or preparations, especially no aluminum salts, especially no ACH and/or AACH (activated aluminum chlorohydrate).

Process-converting products are products by which the process according to the invention is accomplished by means of their use.

Furthermore, a major advantage of the process-converting products is that, compared to the antiperspirants based on aluminum salts, no discolorations at all appear on the skin or clothing. So-called whitening does not occur, nor do the residues that can be observed in textiles resting directly on the underarm skin after repeated wearing and washing.

The silicates can be incorporated in a simple manner into phase 1 required for the process according to the invention. Preferably, they are added as a silicate-containing solution to the other constituents of phase 1. In this case, the proportion of the silicate-containing solution can amount to up to 98% of the total amount of the formulation. In the simplest case, only a thickener and a perfume are added to the silicate solution, wherein perfume is to be understood to mean a mixture comprising one or more individual substances that are olfactorily perceptible.

Accordingly, the process-converting cosmetic products have at least two separate chambers.

Examples are especially dual chamber aerosol containers, dual chamber squeeze bottles, dual chamber containers having a double pump device or roll-on devices (application via a moving body, for example ball or roller), wherein one chamber comprises a silicate-containing phase and the second chamber comprises the pH regulator-containing phase.

Also, one good method is spreading or rubbing by means of planar applicators, which are supplied from a dual chamber container, especially applicators having a flocked and/or textile surface, since their tendency to clog is low.

An advantage compared to aluminum chlorohydrate-containing AP sprays is that the silicates in phase 1 are present in a dissolved state and need not be resuspended by shaking prior to using the spray. The likelihood of the zozzles clogging is reduced as a result.

Furthermore, use in accordance with the process in dual chamber roll-ons and dual chamber pump sprays is possible and advantageous.

Pump sprays provide, like the aerosol sprays, a contactless application of the AP preparation to the skin. However, in the case of pump sprays, it is possible to dispense with pressure-tight containers. Dual chamber pump sprays can be designed to be metal-free, more particularly aluminum-free. For example, PE, PP or PET containers sealed with one or two metal-free spray pump(s) are advantageous, metal-free meaning that the pumped preparation does not come into contact with metallic components. Depending on whether only one pump is used or two pumps are used, the feed is effected via one or two riser tubes and the mixing of the NPK-containing preparation (phase 1) with the base (phase 2) takes place before or after the pump/pumps.

Aerosol spray: The silicates (phase 1) are used in the antiperspirant formulations according to the invention preferably in an amount of from 0.1 to 15% by weight, calculated as $SiO_2$, based on the total mass of the preparation, i.e., including the propellants optionally present. Concentrations of from 0.5 to 5% by weight are especially advantageous.

In the context of the invention, the content of silicon/silicon compounds is specified and calculated as $SiO_2$ content, since the silicon does not exist in the phases and in the mixture as a homogeneous compound. The $SiO_2$ content can be readily determined gravimetrically, for example by ashing.

Active ingredient solution denotes the sum of all constituents without the propellant, since the propellant is generally added only during filling.

In the context of the invention, it is also the case that the phases comprising silicates (phase 1) or the pH regulators (phase 2) comprise cosmetic excipients, as are customarily used in cosmetic preparations, e.g. preservatives, preservation aids, bactericides, perfumes, UV filters, antioxidants, water-soluble vitamins, minerals, suspended solid particles, antifoams, dyes, pigments having a coloring effect, thickening agents, moisturizers and/or humectants or other customary constituents of a cosmetic or dermatological formulation such as electrolytes, organic solvents, alcohols, polyols, emulsifiers, polymers, foam stabilizers or silicone derivatives.

Preference is given to preparing and using the preparations in a visually appealing transparent manner.

Phase 2 is advantageously characterized in that it is in the form of an aqueous or aqueous alcoholic solution or an anhydrous preparation.

Deodorants may also be added advantageously to phase 1 and phase 2.

Different modes of action form the basis of customary cosmetic deodorants. The use of antimicrobial substances as cosmetic deodorants can reduce the bacterial flora on the skin. In this connection, only the odor-causing microorganisms should ideally be reduced in an effective manner. Sweating itself is not influenced as a result; ideally, only the microbial decomposition of sweat is temporarily stopped. The combination of astringents with antimicrobial substances in the same composition is common too.

All active ingredients common as deodorants can be advantageously used, for example odor-masking agents such as common perfume constituents, odor absorbers, for example the phyllosilicates described in DE 40 09 347, including in particular montmorillonite, kaolinite, illite, beidellite, nontronite, saponite, hectorite, bentonite, smectite, additionally for example zinc salts of ricinoleic acid. Antipathogens are likewise suitable for being incorporated into the preparations according to the invention. Advantageous substances are, for example, 2,4,4'-trichloro-2'-hydroxydiphenyl ether (irgasan), 1,6-bis(4-chloro-phenylbiguanido)hexane (chlorhexidine), 3,4,4'-trichlorocarbanilide, quaternary ammonium compounds, clove oil, mint oil, thyme oil, triethyl citrate, farnesol (3,7,11-trimethyl-2,6,10-dodecatrien-1-ol), ethylhexylglycerol, phenoxyethanol, piroctone olamine, caffeine and also the effective agents described in DE 37 40 186, DE 39 38 140, DE 42 04 321, DE 42 29 707, DE 42 29 737, DE 42 37 081, DE 43 09 372, DE 43 24 219. Sodium bicarbonate can be advantageously used too.

Similarly, an antimicrobial silver citrate complex, as described in DE 202008014407, can preferably be used as deodorizing constituent in conjunction with LPSs.

Phase 1 and/or phase 2 preferably also comprise polymers. The polymers preferably originate from the field of the celluloses and/or the polystyrenes. Advantageously, they have been hydrophobically or hydrophilically modified. They serve to adjust the viscosity of the phases and facilitate the pumpability and miscibility and also the draining and distribution behavior on the skin.

The customary cosmetic ingredients of phase 2 of the product according to the invention, in addition to water, ethanol and isopropanol, glycerol and propylene glycol, may also be skincare lipids or lipoids and also oils, such as decyl oleate, cetyl alcohol, cetylstearyl alcohol and 2-octyldodecanol, in the proportions customary for such preparations, and also mucilaginous and film-forming substances and thickening agents, e.g. hydroxyethylcellulose or hydroxypropylcellulose, polyacrylic acid, polyvinylpyrrolidone and waxes.

From the emulsifiers known for cosmetic preparations, these have been found to be advantageous for the preparations of phase 2 usable according to the invention:

polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan trioleate, polyglyceryl-10 stearate, polyglyceryl-4 caprate, lauryl glucoside, polyglyceryl-2 dipolyhydroxylstearate, polyglyceryl-10 laurate, polyglyceryl-4 laurate, decyl glucoside, propylene glycol isostearate, glycol stearate), glyceryl isostearate), sorbitan sesquioleate, glyceryl stearate, lecithin, sorbitan oleate, sorbitan monostearate NF, sorbitan stearate, sorbitan isostearate, steareth-2, oleth-2, glyceryl laurate, ceteth-2, PEG-30 dipolyhydroxystearate, glyceryl stearate SE, sorbitan stearate (and) sucrose cocoate, PEG-4 dilaurate, PEG-8 dioleate, sorbitan laurate, PEG-40 sorbitan peroleate, laureth-4, PEG-7 glyceryl cocoate, PEG-20 almond glycerides, PEG-25 hydrogenated castor oil, stearamide MEA, glyceryl stearate+PEG-100 stearate, polysorbate 85, PEG-7 olivate, cetearyl glucoside, PEG-8 oleate, polyglyceryl-3 methylglucose distearate, PEG-10 stearate, oleth-10, oleth-10/polyoxyl 10 oleyl ether NF, ceteth-10, PEG-8 laurate, ceteareth-12, cocamide MEA, polysorbate 60 NF, polysorbate 60, PEG-40 hydrogenated castor oil, polysorbate 80, isosteareth-20, PEG-60 almond glycerides, polysorbate 80 NF, PEG-150 laurate, PEG-20 methyl glucose sesquistearate, ceteareth-20, oleth-20, steareth-20, steareth-21, ceteth-20, isoceteth-20, PEG-30 glyceryl laurate, polysorbate 20, polysorbate 20 NF, laureth-23, PEG-100 stearate, steareth-100, PEG-80 sorbitan laurate.

Preference is given to using glyceryl isostearate, glyceryl stearate, steareth-2, ceteareth-20, steareth-21, PEG-40 hydrogenated castor oil, PEG-10 stearate, isoceteth-20, isosteareth-20 and ceteareth-12.

Known as solubilizers, but usable as emulsifiers for the preparations of phase 2 usable according to the invention, PEG-40 hydrogenated castor oil, polysorbate 80, laureth-23, PEG-150 laurate and PEG-30 glyceryl laurate can additionally be preferably selected.

In addition to or instead of nonionic emulsifiers, cationic emulsifiers are also suitable for generating stable formulations with the polyquaternium polymers according to the invention. Preferred suitable cationic emulsifiers can be selected from the group consisting of cetrimonium chloride, palmitamidopropyltrimonium chloride, quaternium-87, behentrimonium chloride, distearoylethyl dimonium chloride, distearyldimonium chloride, stearamidopropyl dimethylamine and/or behentrimonium methosulfate.

It is likewise advantageous to add customary antioxidants to the preparations of phase 2 in the context of the present invention. According to the invention, favorable antioxidants which can be used are all antioxidants that are suitable or customary for cosmetic and/or dermatological uses.

The amount of antioxidants (one or more compounds) in the preparations is preferably from 0.001 to 30% by weight, particularly preferably from 0.05 to 20% by weight, more particularly from 1 to 10% by weight, based on the total weight of the preparation.

If the cosmetic or dermatological preparation of phase 2 is a solution or emulsion or dispersion, it is possible to use as solvents, consistency regulators and/or active skincare ingredients:

water or aqueous solutions oils, such as triglycerides of capric acid or of caprylic acid and alkyl benzoate, but preferably cyclic silicone oils or readily volatile hydrocarbons;

fats, waxes and other natural and synthetic lipids, preferably esters of fatty acids with alcohols of low carbon number, for example with isopropanol, propylene glycol or glycerol, or esters of fatty alcohols with alkanoic acids of low carbon number or with fatty acids; vegetable oils such as, for example, avocado oil, cuckoo flower oil, olive oil, sunflower oil, rapeseed oil, almond oil, evening primrose oil, coconut oil, palm oil, linseed oil, shea butter.

alcohols, diols or polyols of low carbon number, and also the ethers thereof, more particularly propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

skincare substances such as, for example, panthenol, allantoin, urea, urea derivatives, guanidine, ascorbic acid, glycerylglucose.

In particular, mixtures of the aforementioned ingredients are used. In the case of alcoholic solvents, water may be a further constituent.

Suitable as propellant for cosmetic and/or dermatological preparations in the context of the present invention that are sprayable from aerosol containers are the readily volatile, liquefied propellants that are customary and known, for example hydrocarbons (propane, butane, isobutane), which can be used alone or in a mixture with one another. Dimethyl ether, nitrous oxide, carbon dioxide, nitrogen and compressed air can be advantageously used too.

A person skilled in the art is of course aware that there are inherently nontoxic propellants which would be suitable in principle for the realization of the present invention in the form of aerosol preparations, but which should nevertheless be dispensed with because of environmental unfriendliness or other concomitants, especially fluorinated hydrocarbons and chlorofluorocarbons (CFCs).

In the case of the aerosol preparations, oils miscible in the active-ingredient solution with the propellant (propane, butane, isobutane) are added in many cases, since an oil which is immiscible leads to precipitates, which in a glass aerosol container result in it no longer being possible to shake up the active-ingredient particles.

Cosmetic preparations of phase 2 can also be present as gels containing not only an effective content of the active ingredient according to the invention and solvents customarily used therefor, preferably water, but also organic thickening agents (thickeners), for example tamarind flour, konjac mannan, guar gum, hydroxypropyl guar, locust bean gum flour, gum arabic, xanthan gum, sodium alginate, cellulose derivatives, preferably methylcellulose, hydroxymethylcellulose, hydroxyethylcellulose, hydroxypropylcellulose, hydroxypropylmethylcellulose, carboxymethylcellulose or a mixture of polyethylene glycol and polyethylene glycol stearate or distearate. The thickening agent is present in the formulation for example in an amount between 0.1 and 40% by weight, preferably between 0.5 and 25% by weight.

Apart from that, the customary measures for putting together cosmetic formulations must be observed, which measures are familiar to a person skilled in the art.

DETAILED DESCRIPTION OF EMBODIMENTS OF THE INVENTION

What follows are advantageous exemplary embodiments of the present invention.

The following examples illustrate the phases that can be used for the process according to the invention, mixtures thereof and application for reducing or preventing sweating.

The numerical data are proportions by weight, based on the total mass of the mixture.

|  | 1 | 2 | 3 | 4 | 5 | 6 |
|---|---|---|---|---|---|---|
| Phase 1 |  |  |  |  |  |  |
| Sodium silicate (Sigma 338443) [g] | 11.2 | 11.2 | 11.2 | 11.2 | 11.2 | 11.2 |
| Phase 2 |  |  |  |  |  |  |
| NaOH, 45% [g] | 0.89 | 0.89 | 0.89 | 0.89 | 0.89 | 0.89 |
| Citric acid [g] | 3.55 | 4.97 | 4.62 | 4.26 | 6.66 | 6.66 |
| H2O [g] | 84.36 | 82.94 | 83.29 | 83.65 | 81.25 | 72.37 |
| EtOH [g] |  |  |  |  |  | 8.88 |
| pH component 2 | 3.10 | 2.80 | 2.84 | 2.91 | 2.70 | 2.70 |
| Sum of phase 1 and 2 | 100 | 100 | 100 | 100 | 100 | 100 |
| pH of the mixture of phase 1 and 2 | 6.4 | 5.1 | 5.3 | 5.5 | 4.2 | 4.4 |

|  | Data in % by weight | | | | | |
|---|---|---|---|---|---|---|
|  | 7 | 8 | 9 | 10 | 11 | 12 |
| Phase 1 |  |  |  |  |  |  |
| Sodium silicate (Sigma 338443) | 11.2 | 11.2 | 11.2 | 11.2 | 11.2 | 11.2 |
| Phase 2 |  |  |  |  |  |  |
| Water (demineralized) | 58.2 | 36.84 | 47.49 | 49.06 | 48.25 | 78.25 |
| Ethanol | 20 | 30 | 10 | 25 | 30 |  |
| Glycerol |  |  | 11 |  |  |  |
| PEG-200 (Sigma) |  |  |  | 20 |  |  |
| Citric acid (citric acid monohydrate, Jungbunzlauer) | 4.26 | 4.62 | 4.97 | 3.55 | 4.26 | 4.26 |
| Sodium hydroxide | 0.89 | 0.89 | 0.89 | 0.89 | 0.89 | 0.89 |
| Persea gratissima oil (IMCD Germany) | 0.1 | 0.1 | 0.1 | 0.1 | 0.1 | 0.1 |
| PEG-40 hydrogenated castor oil (Eumulgin CO 40; BASF) | 2 | 2 | 2 | 2 | 2 | 2 |
| Perfume | 1 | 1 | 1 | 1 | 1 | 1 |
| Hydroxyethylcellulose (Natrosol 250 HHX pharm; Ashland) | 0.35 | 0.35 | 0.35 | 0.2 |  |  |
| Xanthan gum (Keltrol CG-F, Rahn) |  |  |  |  | 0.3 | 0.3 |
| PEG-8 (Kollisolv PEG 400, BASF) | 2 | 2 | 2 | 2 | 2 | 2 |
| Sum of phase 1 and 2 | 100 | 100 | 100 | 100 | 100 | 100 |
| pH of the mixture | 5.5 | 5.3 | 5.1 | 6.4 | 5.5 | 5.5 |

| | Data in % by weight | | | | | |
|---|---|---|---|---|---|---|
| | 13 | 14 | 15 | 16 | 17 | 18 |
| Phase 1 | | | | | | |
| Sodium silicate (Sigma 338443) | 11.12 | 11.12 | 11.12 | 11.12 | 11.12 | 11.12 |
| Phase 2 | | | | | | |
| Water (demineralized) | 58.63 | 37.27 | 36.57 | 48.99 | 43.63 | 68.63 |
| Ethanol | 20 | 30 | 20.35 | 10.35 | 30 | |
| Glycerol | | 11 | 21 | | 5 | |
| PEG-200 (Sigma) | | | | 20 | | 10 |
| Citric acid (citric acid monohydrate, Jungbunzlauer) | 4.26 | 4.62 | 4.97 | 3.55 | 4.26 | 4.26 |
| Sodium hydroxide | 0.89 | 0.89 | 0.89 | 0.89 | 0.89 | 0.89 |
| Persea gratissima oil (IMCD Germany) | 0.1 | 0.1 | 0.1 | 0.1 | 0.1 | 0.1 |
| PEG-40 hydrogenated castor oil (Eumulgin CO 40; BASF) | 2 | 2 | 2 | 2 | 2 | 2 |
| Perfume | 1 | 1 | 1 | 1 | 1 | 1 |
| PEG-8 (Kollisolv PEG 400, BASF) | 2 | 2 | 2 | 2 | 2 | 2 |
| Sum of phase 1 and 2 | 100 | 100 | 100 | 100 | 100 | 100 |
| pH of the mixture | 5.5 | 5.3 | 5.1 | 6.4 | 5.5 | 5.5 |

| Formulation with an O/W emulsion | Data in % by weight | | | |
|---|---|---|---|---|
| prepared cold as second component | 19 | 20 | 21 | 22 |
| Phase 1 | | | | |
| Sodium silicate | 11.2 | 11.2 | 11.2 | 11.2 |
| Phase 2 | | | | |
| Water | 50.44 | 55.24 | 40.44 | 37.27 |
| Ethanol | 21.22 | 15 | 20.15 | 3.68 |
| Citric acid (citric acid monohydrate, Jungbunzlauer) | 3.55 | 4.97 | 4.62 | 4.26 |
| Sodium hydroxide | 0.89 | 0.89 | 0.89 | 0.89 |
| Glycerol | 2 | 2 | 12 | 12 |
| PEG-200 (Sigma) | | | | 20 |
| Benzyl alcohol | 0.3 | 0.3 | 0.3 | 0.3 |
| Phenoxyethanol | 0.5 | 0.5 | 0.5 | 0.5 |
| Xanthan gum (Keltrol CG-F, Rahn) | 0.3 | 0.3 | 0.3 | 0.3 |
| Lauryl glucoside, polyglyceryl-2 dipolyhydroxystearate, glycerol (Eumulgin VL 75, BASF) | 2 | 2 | 2 | 2 |
| C12-15 alkyl benzoate (Cetiol AB, BASF) | 3 | 3 | 3 | 3 |
| Octyldodecanol (Eutanol G, BASF) | 2 | 2 | 2 | 2 |
| Caprylic/capric triglyceride (Myritol 312, BASF) | 2 | 2 | 2 | 2 |
| Hydroxyethylcellulose (Natrosol 250 HHX pharm; Ashland) | 0.1 | 0.1 | 0.1 | 0.1 |
| Perfume | 0.5 | 0.5 | 0.5 | 0.5 |
| Sum of phase 1 and 2 | 100 | 100 | 100 | 100 |
| pH of the mixture | 6.4 | 5.1 | 5.3 | 5.5 |

| Formulation with an O/W emulsion | Data in % by weight | | | | |
|---|---|---|---|---|---|
| prepared cold as second component | 23 | 24 | 25 | 26 | 27 |
| Phase 1 | | | | | |
| Sodium silicate | 11.12 | 11.12 | 11.12 | 11.12 | 11.12 |
| Phase 2 | | | | | |
| Water | 50.89 | 40.89 | 39.89 | 41.53 | 43.51 |
| Ethanol | 19.88 | 11.3 | 20.23 | 30 | 23.68 |
| Citric acid (citric acid monohydrate, Jungbunzlauer) | 4.97 | 3.55 | 4.62 | 4.26 | 3.55 |
| NaOH | 0.89 | 0.89 | 0.89 | 0.89 | 0.89 |
| Glycerol | | | 11 | | 5 |
| PEG-200 (Sigma) | | 20 | | | |
| Benzyl alcohol | 0.3 | 0.3 | 0.3 | 0.3 | 0.3 |
| Phenoxyethanol | 0.5 | 0.5 | 0.5 | 0.5 | 0.5 |
| Cocamidopropylamine oxide (Amphotensid COX/C, Zschimmer & Schwarz) | 10 | 10 | 10 | 10 | 10 |

| | | | | | |
|---|---|---|---|---|---|
| Persea gratissima oil | 0.1 | 0.1 | 0.1 | 0.1 | 0.1 |
| Hydroxyethylcellulose | 0.35 | 0.35 | 0.35 | 0 | 0.35 |
| Xanthan gum (Keltrol CG-F, Rahn) | | | | 0.3 | |
| Perfume | 1 | 1 | 1 | 1 | 1 |
| Sum of phase 1 and 2 | 100 | 100 | 100 | 100 | 100 |
| pH of the mixture | 5.1 | 6.4 | 5.3 | 5.5 | 6.4 |

| Formulation with an O/W emulsion | Data in % by weight | | | | |
|---|---|---|---|---|---|
| (prepared hot) as second component | 28 | 29 | 30 | 31 | 32 |
| Phase 1 | | | | | |
| Sodium silicate | 11.2 | 11.2 | 11.2 | 11.2 | 11.2 |
| Phase 2 | | | | | |
| Water | 40 | 43.65 | 34.36 | 28.94 | 36.65 |
| Sodium hydroxide, 45% | 0.89 | 0.89 | 0.89 | 0.89 | 0.89 |
| Citric acid (citric acid monohydrate, Jungbunzlauer) | 4.62 | 4.26 | 3.55 | 4.97 | 4.26 |
| Panthenol | 0.3 | 0.3 | 0.3 | 0.3 | 0.3 |
| Ethanol | | | 10 | 5 | |
| Glycerol | 3.29 | 0 | 0 | 9 | 7 |
| Persea gratissima oil | 0.3 | 0.3 | 0.3 | 0.3 | 0.3 |
| Caprylic/capric triglyceride (Myritol 312, BASF) | 10 | 10 | 10 | 10 | 10 |
| Steareth-21 (Tego Alkanol S 21, Evonik Industries) | 6.7 | 6.7 | 6.7 | 6.7 | 6.7 |
| Steareth-2 (Tego Alkanol S2, Evonik Industries) | 11.7 | 11.7 | 11.7 | 11.7 | 11.7 |
| Trisodium EDTA, 20% (Edeta BS, BASF) | 5 | 5 | 5 | 5 | 5 |
| Benzyl alcohol | 1 | 1 | 1 | 1 | 1 |
| Phenoxyethanol | 1.7 | 1.7 | 1.7 | 1.7 | 1.7 |
| Perfume | 3.3 | 3.3 | 3.3 | 3.3 | 3.3 |
| Sum of phase 1 and 2 | 100 | 100 | 100 | 100 | 100 |
| pH of the mixture | 5.3 | 5.5 | 6.4 | 5.1 | 5.5 |

Preparation of Phase 2:

The water-soluble constituents are heated together with the amount of water specified to 75° C. The oil components and emulsifiers are heated separately to 75° C. The phases are combined and homogenized. The emulsion is cooled to room temperature while being stirred.

What is claimed is:

1. A method for reducing or preventing apoeccrine sweat formation, wherein the method comprises applying a mixture of a first part preparation which is alkaline and comprises one or more silicates (phase 1) and a second part preparation which is acidic and comprises one or more pH regulators (phase 2) to skin, the mixture having a pH of from 4 to 8 and the time period between mixing the first and second part preparations and applying the mixture to the skin being not more than five minutes.

2. The method of claim 1, wherein the mixture is applied from a multi-chamber container, a first chamber of the multi-chamber container comprising phase 1 and a second chamber of the multi-chamber container comprising phase 2.

3. The method of claim 1, wherein the one or more silicates are one or more alkali metal silicates.

4. The method of claim 3, wherein the one or more silicates comprise sodium silicate.

5. The method of claim 1, wherein phase 1 comprises from 0.1% to 15% by weight of one or more silicon-containing compounds, calculated as $SiO_2$, based on a total mass of the preparation.

6. The method of claim 5, wherein phase 1 comprises from 0.5% to 5% by weight of one or more silicon-containing compounds.

7. The method of claim 1, wherein the one or more pH regulators are selected from buffer systems and unbuffered acids.

8. The method of claim 7, wherein the buffer systems comprise at least one substance from the group 2-aminobutanol, 2-(2-aminoethoxy)ethanol, aminoethylpropanediol, aminomethylpropanediol, aminomethylpropanol, aminopropanediol, bishydroxyethyl tromethamine, butyldiethanolamine, butylethanolamine, dibutylethanolamine, diethanolamine, diethylethanolamine, diisopropanolamine, dimethylaminomethylpropanol, dimethylisopropanolamine, dimethyl MEA, ethanolamine, ethylethanolamine, isopropanolamine, methyldiethanolamine, methylethanolamine, triethanolamine, triisopropanolamine, tromethamine, polyethylenimine, tetrahydroxypropyl ethylenediamine.

9. The method of claim 7, wherein the unbuffered acids comprise at least one substance from the group citric acid, lactic acid, tartaric acid, fatty acids, phosphoric acid, phosphonic acids, polyacrylic acids, succinic acid, malic acid, oxalic acid, amino acids, hydrochloric acid, sulfuric acid, phosphoric acid.

10. The method of claim 1, wherein phase 1 has a pH>9.5.

11. The method of claim 10, wherein the mixture of phase 1 and phase 2 has a pH of from 5.3 to 6.7.

12. The method of claim 1, wherein at least one of phase 1 and phase 2 comprises one or more stabilizers selected from alcohols, diols, and substances having at least three hydroxyl groups.

13. The method of claim 1, wherein phase 1 and phase 2 are free of aluminum chlorohydrate.

14. The method of claim 1, wherein the mixture of first and second part preparations is applied topically as an aerosol or by means of a moving body.

15. A cosmetic product for implementing the method of claim 1, wherein the product comprises a multi-chamber container, wherein a first chamber comprises a preparation comprising one or more silicates (phase 1) and a second chamber comprises a preparation comprising one or more pH regulators (phase 2) and is configured such that during application phases 1 and 2 stored in the first and second chambers are simultaneously withdrawn from the chambers and phases 1 and 2 are mixed on dispensing or shortly before dispensing.

16. The method of claim 1, wherein phase 2 has a pH of from 2.7 to 3.1.

17. The method of claim 1, wherein phase 2 is an aqueous solution.

18. The method of claim 1, wherein phase 2 is an O/W emulsion.

19. The method of claim 1, wherein the mixture of phase 1 and phase 2 has a pH of from 5.1 to 6.9.

20. The method of claim 1, wherein the mixture of phase 1 and phase 2 has a pH of from 5.3 to 6.7.

\* \* \* \* \*